United States Patent
Gilbert et al.

(10) Patent No.: US 7,451,772 B2
(45) Date of Patent: Nov. 18, 2008

(54) ULTRASONIC CLEANING METHOD AND APPARATUS

(75) Inventors: Nicole Gilbert, Charlotte, NC (US); Karen Williams, Matthews, NC (US)

(73) Assignee: Gilwil LLC, Charlotte, NC (US)

( * ) Notice: Subject to any disclaimer, the term of this patent is extended or adjusted under 35 U.S.C. 154(b) by 427 days.

(21) Appl. No.: 11/194,781

(22) Filed: Aug. 1, 2005

(65) Prior Publication Data
US 2007/0023064 A1    Feb. 1, 2007

(51) Int. Cl.
B08B 3/00    (2006.01)
(52) U.S. Cl. .................. 134/135; 134/110; 134/184
(58) Field of Classification Search .......... 134/184, 134/110, 135, 147, 186
See application file for complete search history.

(56) References Cited

U.S. PATENT DOCUMENTS

| | | | |
|---|---|---|---|
| 3,779,707 A | 12/1973 | Tabone | |
| 3,973,760 A | 8/1976 | Browning et al. | |
| 4,870,982 A | 10/1989 | Liu | |
| 5,076,305 A * | 12/1991 | Williams | 134/58 R |
| 5,159,945 A * | 11/1992 | Bannon | 134/85 |
| 5,379,785 A | 1/1995 | Ohmori et al. | |
| 6,143,391 A * | 11/2000 | Barnes et al. | 428/99 |

FOREIGN PATENT DOCUMENTS

| | | |
|---|---|---|
| DE | 3633046 A1 | 1/1988 |
| GB | 2165754 A | 4/1986 |
| GB | 2253457 A | 9/1992 |

OTHER PUBLICATIONS http:/www.brownells.com/aspx/NS/store/ProductDetail.aspx?p=7768&title=ULTRASONIC+CLEANIN . . . .
http:/www.brownells.com/aspx/NS/store/ProductDetail.aspx?p=5539&title=FIREARMS+CLEANING+. . . .
http:/www.labequip.com/itemcatalog/stkno/N491/CREST-690/WITH-HEATER-ULTRASONIC-CLEA . . . .
http:/www.labequip.com/itemcatalog/stkno/N439/BRANSON-DHA-1000/WITH-HEATER-ULTRASO . . . .
http://www.labequip.com/itemcatalog/stkno/N107/BRANSONIC-2510MTH/WITH-HEATER-ULTRAS . . . .
http://www.labequip.com/itemcatalog/stkno/N105/BRANSONIC-8510MTH/WITH-HEATER-ULTRAS . . . .
http://www.codyson.com/cd-6800.html.
http://www.pmrsystems.com/page1.html.
International Search Report & Written Opinion dated Dec. 27, 2006 for international application No. PCT/US2006/029982.

* cited by examiner

Primary Examiner—Michael Barr
Assistant Examiner—Rita R Patel
(74) Attorney, Agent, or Firm—Summa, Allan & Additon, P.A.

(57) ABSTRACT

An apparatus suitable for ultrasonically cleaning objects is disclosed. The apparatus includes a housing and a cleaning chamber within the housing. The apparatus also includes drainer that can be moved between a cleaning position in a lower region of the apparatus and a draining position in an upper region of the apparatus. The drainer is configured to engage at least a portion of the upper region of the housing to thereby position the drainer in the draining position. The apparatus also includes a transducer for transmitting ultrasonic energy into the cleaning chamber.

25 Claims, 2 Drawing Sheets

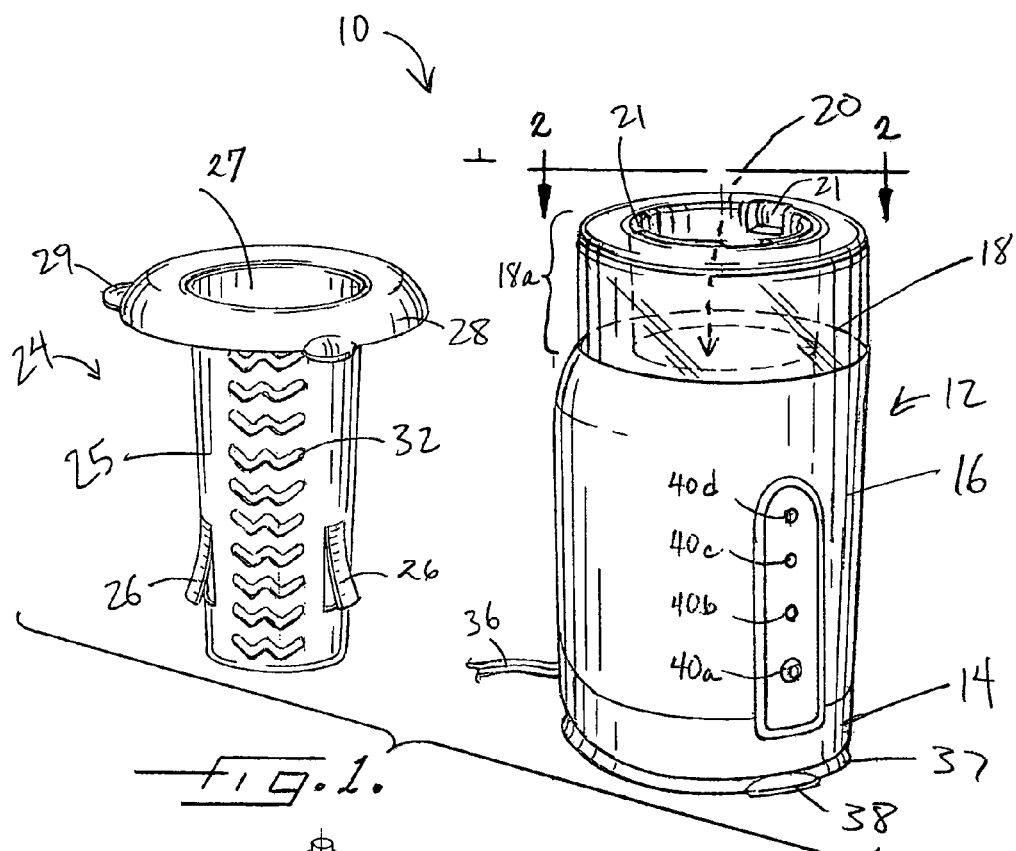
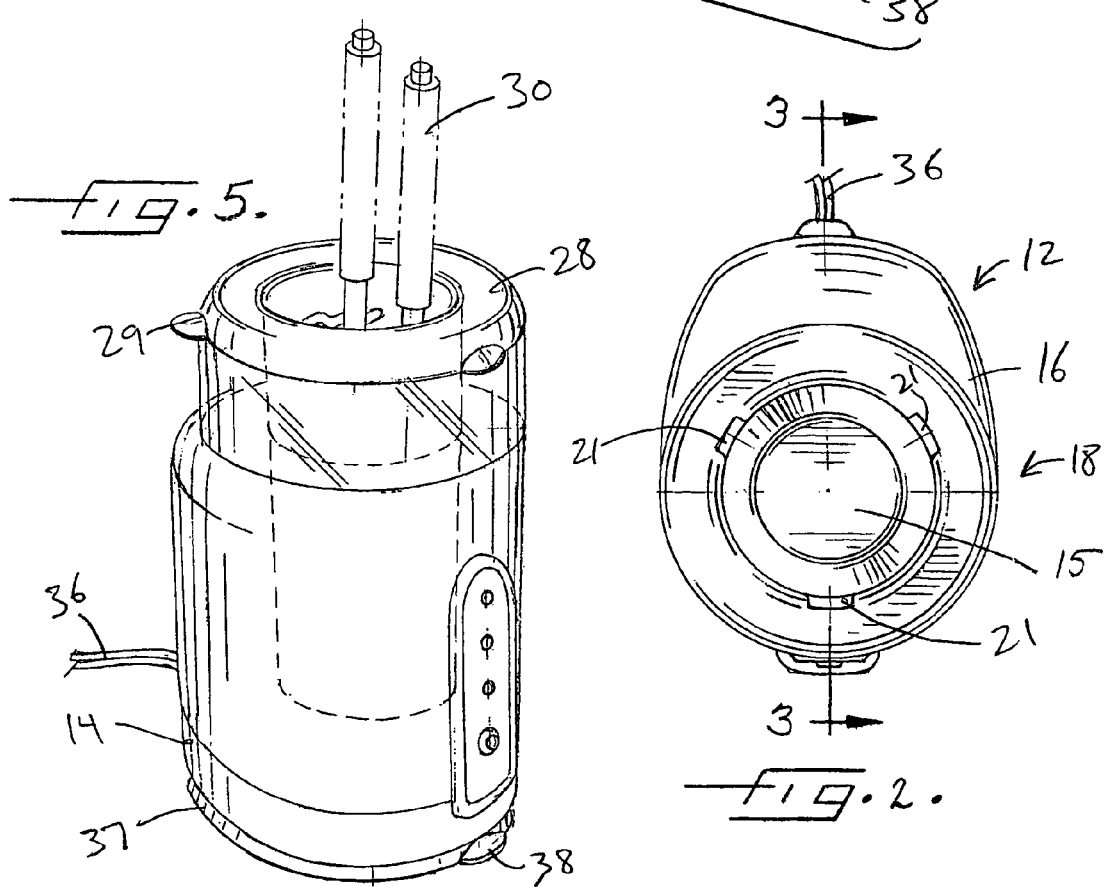

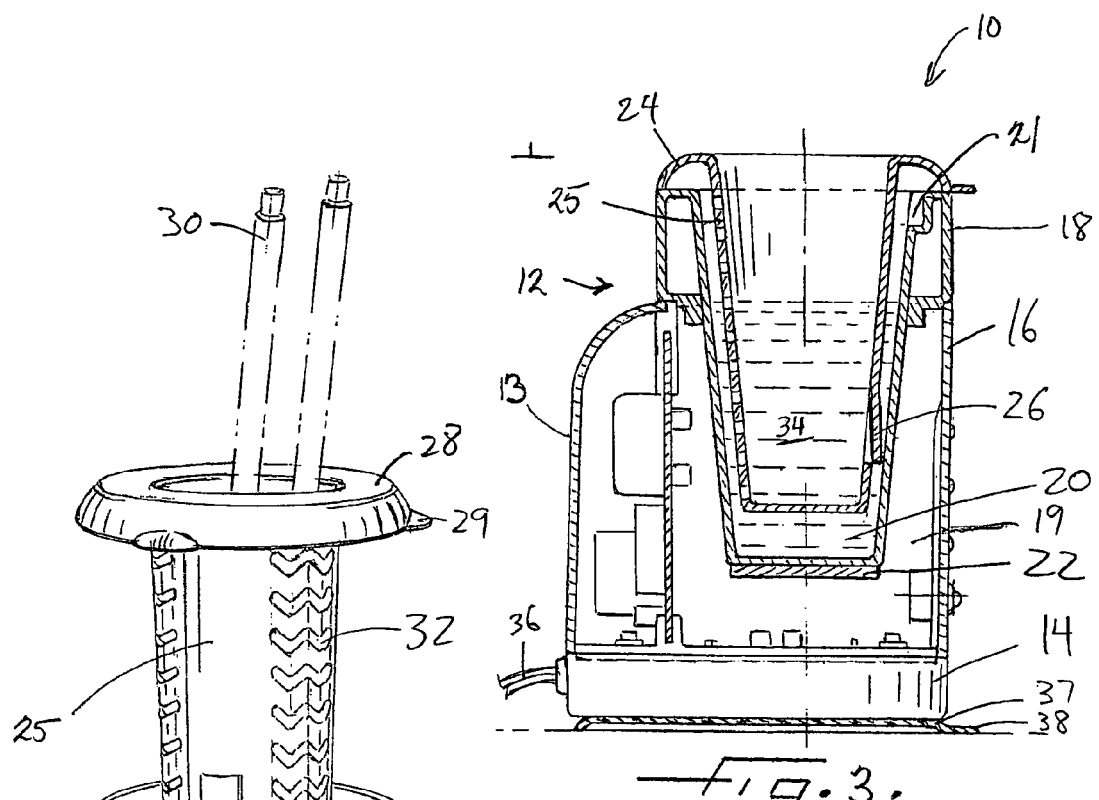
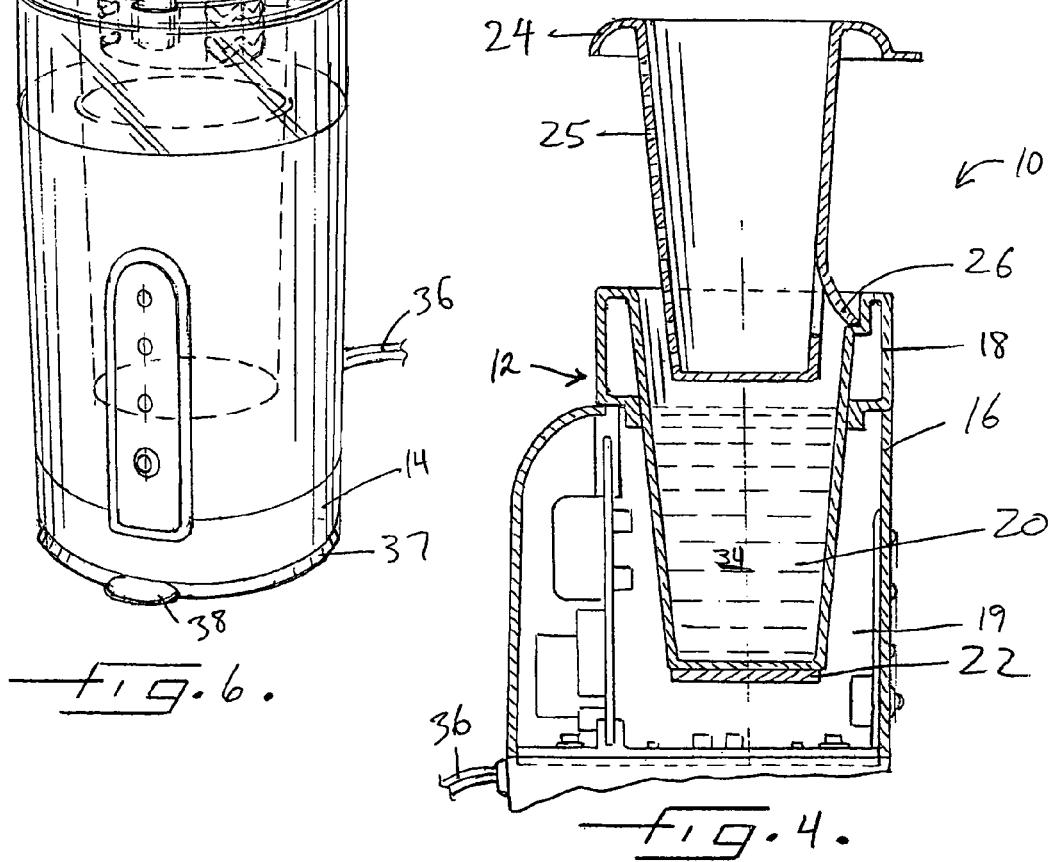

ULTRASONIC CLEANING METHOD AND APPARATUS

BACKGROUND OF THE INVENTION

The present invention relates to an ultrasonic cleaning method and apparatus. More particularly, the invention relates to an ultrasonic cleaning method and apparatus that can utilize heat for a controlled length of time to facilitate the cleaning of various objects, including hair care equipment.

Individuals and professional stylists employ various types of hair care equipment, including curling irons, hair straighteners, and the like, to aid in styling hair. As an example, conventional curling irons typically include a smooth, elongated tubular barrel secured to a handle, with a heating element inside the tube. An unheated clamp extends along a portion of the barrel for the purpose of clamping or holding sections of hair against the round barrel. Heat that is transferred from the heating element to the barrel causes hair which is wrapped around the barrel to retain a curl after the hair is removed from the curling iron. Hair straighteners operate much like curling irons, but typically have smooth mating flat surfaces which act to straighten the hair when compressed against and pulled along the hair.

Often hair styling products, such as hairspray, mousse, gel, and the like, are used in combination with a particular hair styling appliance to achieve a desired end result. Over time, however, such products can accumulate and build up on the surfaces of the appliance, such as the barrel of a curling iron. Product build up can be particularly problematic in a commercial environment in which a professional stylist works with numerous customers.

Various techniques attempt to remove product buildup and other debris from the barrel of a curling iron or other hair styling appliances. Cleaning solutions, including many conventional cleaners marketed for use in cleaning surfaces in the home, can be sprayed onto the barrel area of the curling iron and the barrel thereafter wiped down in an effort to remove the debris. Cleaning solutions, however, can have limited effectiveness in removing heavy product buildup. In addition, cleaning solutions can be messy, and many cleaning solutions can have undesirable odors, fumes, and the like.

Scraping the debris with a knife, razor blade, or other sharp object, can remove particularly heavy product buildup from a curling iron barrel. Scraping debris from a curling iron barrel, however, can be time consuming. Further, scraping an object can damage its finish. In addition, the use of a sharp object such as a knife or razor blade to remove debris can expose the user to possible injury.

BRIEF SUMMARY OF THE INVENTION

The present invention provides an apparatus and method that can be useful for ultrasonically removing debris from a variety of objects. The cleaning apparatus of the invention can have a housing having a base, a side wall extending upwardly from the base, and an upper region. The inner surfaces of the base and the side wall of the housing can define an interior region therein suitable for housing a cleaning chamber. A transducer can be present to transmit ultrasonic energy into the cleaning chamber.

The apparatus of the invention can further include a drainer, which can be inserted into the cleaning chamber. The drainer can be moved vertically within the apparatus between a cleaning position in a lower region of the apparatus and a draining position in an upper region of the apparatus.

One or more objects to be cleaned can be placed into the drainer, before or after the drainer is inserted into the cleaning chamber into the cleaning position. A cleaning cycle can then be activated to remove debris from the objects. One or more visual indicators present along an outer surface of the housing of the apparatus can indicate various stages of the cleaning cycle, including completion of the same.

To assist a user in removing objects from the drainer at the conclusion of a cleaning cycle, the drainer is configured along a portion of a side wall thereof to engage at least a portion of the upper region of the housing. In this manner, the drainer can be mounted within an upper region of the cleaning apparatus in a draining position. In certain embodiments of the invention, the upper region of the housing defines at least one recess, and the side wall of the drainer defines at least one tab dimensioned for insertion into the recess to thereby position the drainer in the draining position.

At the conclusion of a cleaning cycle, a user can lift the drainer upwardly out of the cleaning chamber and mount the drainer in the draining position. In this manner, a user can position the drainer within an upper region of the cleaning apparatus and allow the objects to cool to an appropriate handling temperature. In addition, the side walls of the drainer are typically perforated to allow cleaning fluid, when present, to readily drain from the drainer back into the cleaning chamber.

In certain embodiments of the invention, the drainer can also be configured to hold one or more elongate objects to be cleaned orientated in a generally vertical position within the cleaning chamber. Accordingly, the present invention can be particularly useful for removing hair product build-up on the barrel of a curling iron. The present inventors have found that ultrasonic cleaning of elongate objects in a vertical orientation can effectively and substantially uniformly remove debris from the surface of the object. In contrast, ultrasonic cleaning of objects placed generally horizontally within a cleaning apparatus can result in less uniform removal of debris and can even result in debris redepositing onto another surface of the object.

The cleaning apparatus of the invention can further include a suction cup base. The suction cup base can apply a vacuum seal between the apparatus and a reasonably smooth, level surface, thereby discouraging unintentional movement (e.g., vibration-induced or accidental movement).

The present invention also includes a method of ultrasonically cleaning one or more objects. The method of the invention can include transmitting ultrasonic energy to at least one object in a drainer inserted into a cleaning chamber of a cleaning apparatus under conditions sufficient to remove debris from the object. In the method, the drainer can include a side wall having at least a portion thereof configured to engage at least a portion of an upper region of the cleaning apparatus in a draining position. The method further includes engaging the configured portion of the side wall of the drainer with the corresponding portion of the upper region of the cleaning apparatus.

To assist in the removal of debris, a cleaning fluid can be added to the cleaning chamber prior to the transmission of ultrasonic energy. In certain embodiments of the invention, the method can further include heating the cleaning fluid to a first preset temperature; thereafter activating an ultrasonic energy source to transmit ultrasonic energy to the object to be cleaned within the cleaning chamber; and thereafter allowing the cleaning fluid to cool to a second preset temperature.

The apparatus and method of the present invention accordingly can minimize and even eliminate many of the problems associated with prior cleaning techniques. The invention can minimize the mess, odor, fumes, and the like, associated with spraying a cleaning solution onto the object to be cleaned. The present invention can also allow a user to clean an object while minimizing risk of injury, such as can result from the use of a sharp edge to scrap away debris. Further, the present invention can effectively remove debris with minimal or no damage to the surface finish of the object. Still further, the present invention can be time efficient and can provide additional time savings by allowing a user to effectively clean multiple objects in single cleaning cycle.

BRIEF DESCRIPTION OF THE DRAWINGS

Having thus described the invention in general terms, reference will now be made to the accompanying drawings, which are not necessarily drawn to scale, and in which:

FIG. 1 is a perspective view of an exemplary cleaning apparatus including a housing and a drainer in accordance with one embodiment of the invention;

FIG. 2 is a top view of the cleaning apparatus of FIG. 1 taken along line 2-2;

FIG. 3 is a cross-sectional view of the cleaning apparatus of FIGS. 1 and 2 taken along line 3-3 illustrating the drainer in a cleaning position;

FIG. 4 is a cross-sectional view of the cleaning apparatus of FIGS. 1 and 2 illustrating the drainer in a draining position;

FIG. 5 is a perspective view of the cleaning apparatus of the invention including an object to be cleaned with the drainer in a cleaning position; and FIG. 6 is a perspective view of the cleaning apparatus of the invention including an object to be cleaned with the drainer in a draining position.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout the specification.

In one aspect of the invention as depicted in FIG. 1, the invention can include an apparatus 10 suitable for ultrasonically cleaning objects. Generally, the ultrasonic cleaning apparatus of the invention utilizes sound waves in a fluid medium to clean surface debris from an article. The invention can be useful for ultrasonically cleaning a variety of elongate shaped objects, including without limitation hairdressing equipment, such as curling irons; firearms parts; barbeque and other cooking utensils; hand tools; and other similarly shaped objects.

The apparatus 10 includes a housing 12 having a base 14, a side wall 16 extending upwardly from the base 14, and an upper region 18. The inner surfaces of the base 14 and the side wall 16 can define a region within the housing 12 that is suitable for housing a cleaning chamber 20, as illustrated in FIGS. 3 and 4.

The housing 12 can further include an opening 15 along a top surface thereof. The opening 15 is adapted for receiving one or more objects to be cleaned into the cleaning chamber 20, which object(s) are generally contained within a drainer 24, as discussed in more detail below. The opening 15 can have any shape and/or size suitable for receiving the object(s) to be cleaned, such as the generally circular shape illustrated in FIG. 2.

The housing 12 can have a generally cylindrical shape as illustrated. The present invention, however, is not limited to this configuration, and accordingly the housing 12 can have any of a variety of suitable shapes. For example, the housing 12 can include four side walls positioned to form a generally rectangular or cube shape. In addition, as generally indicated at 13 in FIG. 3, the housing 12 can have one or more protrusions extending generally outwardly from and/or along at least a portion of the outer surface of the housing. The protrusion 13 can be useful, for example, for housing various electronic components, displaying visual indicators, and the like. In addition, the outer surface of the protrusion 13 can be contoured to form a gripping surface to permit a user to more securely grip the apparatus when moving and/or holding the same. Accordingly, as used herein, reference to the side wall 16 of the housing 12 includes any wall configuration creating an internal region thereof suitable for housing a cleaning chamber 20, including without limitation a single continuous wall forming a substantially cylindrical shaped housing, four walls forming a generally cube or rectangular shaped housing, and the like, as well as any such configuration modified by one or more protrusions.

The upper region 18 of the housing 12 may be constructed of a transparent material (e.g., transparent plastic, or the like) as indicated by the brackets 18a in FIG. 1. Use of a transparent material in this region can allow a user to visually observe the interior of the housing 12. This can be helpful, for example, to prevent overfilling the cleaning chamber 20 with a cleaning fluid, as indicated at 34, when present. Appropriate cleaning fluids are known to those skilled in the art and are commercially available. Exemplary cleaning fluids useful in the present invention include, but are not limited to, water, water-based cleaning solutions, and organic-based cleaning solutions. As used herein, the term "cleaning fluid" can also include air (i.e., in those embodiments of the invention in which the cleaning cycle does not include the use of a liquid cleaning solution).

The cleaning chamber 20 located within the housing 12 can be dimensioned to accommodate one or more substantially elongate objects to be cleaned in a generally vertical orientation, which objects, as noted above, are generally contained within a drainer 24. As a non-limiting example, the cleaning chamber 20 can have a generally cylindrical configuration, such as illustrated in FIGS. 3 and 4. In the exemplary embodiment of the invention illustrated in FIGS. 3 and 4, the cleaning chamber 20 can further have a first diameter at an upper region thereof and a second diameter at a lower region thereof that is smaller than the first diameter. In this embodiment of the invention, the cleaning chamber 20 can form a generally tapered cylindrical shape.

The present invention, however, is not limited to this configuration, and accordingly, the cleaning chamber 20 can have any of a variety of suitable shapes dimensioned for holding the objects to be cleaned, and in exemplary embodiments of the invention, holding one or more substantially elongate objects to be cleaned in a generally vertical orientation. Exemplary embodiments of the cleaning apparatus of the invention can accordingly include a cleaning chamber having a single continuous side wall forming a substantially cylindrical shaped housing, four side walls forming a generally cube or rectangular shaped housing, and the like.

The cleaning chamber can be formed of any of a variety of materials suitable for use in an ultrasonic cleaning operation. As discussed in more detail herein, the invention can include the use of a cleaning fluid, and accordingly, in certain embodiments of the invention, the cleaning chamber 20 can be formed of a material substantially impervious to undesired effects of the cleaning fluid (such as rusting). In exemplary embodiments of the invention, the cleaning chamber 20 can be formed of stainless steel.

The apparatus of the invention can further include a transducer 22 for transmitting ultrasonic energy into the cleaning chamber 20. As illustrated in FIGS. 3 and 4, in certain embodiments of the invention, the transducer 22 can be positioned along an outer bottom surface of the cleaning chamber 20. In this embodiment of the invention, the transducer 22 can be attached to the outer bottom surface of the cleaning chamber 20 using means known in the art for attaching a transducer to an object that minimizes or eliminates interference with the transmission of ultrasonic energy by the transducer. As a non-limiting example, the transducer 22 can be adhered to the outer bottom surface of the cleaning chamber 20 using a suitable adhesive, such as an epoxy adhesive, as is known in the art.

The location of the transducer can vary, and accordingly the apparatus 10 of the invention can also include a transducer 22 positioned in other regions of the housing 12, so long as the transducer functions to transmit ultrasonic energy into the cleaning chamber in a manner sufficient to assist in the removal of debris from one or more objects placed within the chamber. As another non-limiting example, the apparatus 20 can include at least one or more transducer(s) positioned along one or more outer side wall surface(s) of the cleaning chamber 20. In this embodiment of the invention, the apparatus 20 can include at least two transducers positioned along opposing outer side wall surfaces of the cleaning chamber 20, optionally in combination with the at least one transducer 22 positioned along the outer bottom surface of the cleaning chamber 20.

The transducer 22 can be selected from any of the types of transducers known in the art and are readily commercially available. The transducer 22 can be a piezoelectric transducer, which can convert electrical energy to mechanical energy using a vibrating element, typically made of ceramic materials, to amplify and direct the mechanical energy into a fluid medium. Magnetostrictive transducers, which generally utilize an alternating magnetic field to induce mechanical vibrations in the ultrasonic frequency range, can also be useful in the present invention.

The apparatus 10 of the invention can further include a heating element (not shown) suitable for heating the interior of the cleaning chamber and/or heating a cleaning fluid 34 when present in the cleaning chamber. The heating element can heat the cleaning fluid 34 to enhance its cleaning effect on the object 30.

The heating element can be in the form of a sheet material that forms a sleeve surrounding a substantial portion of the outer surface of the cleaning chamber 20. The heating element optionally can be secured to an outer surface of the cleaning chamber 20 using a suitable adhesive, such as a pressure sensitive adhesive. Sheet materials suitable for use as a heating element are also known in the art and are commercially available.

The apparatus can further include an insulating sleeve (not shown) formed, for example, of a fiberglass insulating sheet material. The insulating sleeve can be positioned along the outer surface of the heating element to thereby sandwich the heating element between the insulating sleeve and the cleaning chamber. In this manner, the insulating element can assist in the efficient operation of the heating element by minimizing heat loss.

Turning again to FIG. 1, the apparatus 10 of the invention can further include a drainer 24. FIG. 1 illustrates an exemplary embodiment of the invention in which the drainer 24 is a separate component from the housing 12. The present invention is not limited to this embodiment of the invention, and accordingly the cleaning apparatus can include a drainer 24 which is an integral part of the housing 12.

The drainer 24 is dimensioned to allow the ready insertion and/or removal of the drainer 24 into and out of the cleaning chamber 20. In addition, the drainer 24 can be dimensioned to accommodate one or more generally elongate shaped objects in a substantially vertical orientation, such as one or more curling irons 30, as illustrated in FIGS. 5 and 6. Furthermore, the dimensions of the drainer 24 and/or the material(s) used to make the drainer 24 can be selected so that the drainer 24 can adapt to the shape of the cleaning chamber 20 when the drainer is inserted into the chamber, such as the cleaning position illustrated in FIG. 3.

In an exemplary embodiment of the invention, the drainer 24 can be formed of a resilient material. The resilient material can be a thermoplastic material, such as a polyolefin, including polypropylene, polyethylene, and co- and terpolymers and blends thereof; a polyester; and the like. Advantageously, the drainer 24 is formed of a resilient material having a sufficiently high melting point to prevent substantial deformation and/or softening of the drainer at operating temperatures.

Many conventional ultrasonic cleaners are shaped to allow placement of the object to be cleaned in a generally horizontal position. The present inventors, however, have found that ultrasonic cleaning of elongate objects in a vertical orientation can provide effective and substantially uniform removal of debris from substantially the entire surface of the object. In contrast, ultrasonic cleaning of objects placed generally horizontally within a cleaning apparatus can result in less uniform removal of debris and even redeposit debris onto another surface of the object.

In the exemplary embodiment of the invention illustrated in FIGS. 1, 3, and 4, the drainer 24 can include a side wall 25 defining a substantially cylindrical shape having an opening 27 for receiving one or more objects 30 to be cleaned. Also in the exemplary embodiment of the invention illustrated in FIGS. 1, 3 and 4, the drainer 24 can have a first diameter at an upper region thereof and a second diameter at a lower region thereof that is smaller than the first diameter of the drainer. In this embodiment of the invention, the drainer 20 can form a generally tapered cylindrical shape.

The present invention, however, is not limited to the illustrated configuration for the drainer 24, and accordingly, the drainer 24 can have any of a variety of suitable shapes dimensioned for holding the objects to be cleaned, and in exemplary embodiments of the invention, for holding one or more substantially elongate objects to be cleaned in a generally vertical orientation. As additional non-limiting examples, exemplary embodiments of the invention include a drainer 24 having a single continuous side wall forming a substantially cylindrical shaped housing, four side walls forming a generally rectangular shaped housing, and the like.

As illustrated in FIG. 1, the side wall(s) 25 of the drainer 24 can further include one or more perforations or openings 32 therein to allow the passage of a fluid, such as a cleaning fluid, into and out of the drainer 24. The perforations can be present as a substantially uniform or random pattern covering at least a portion, and in certain embodiments substantially the entire surface, of the side wall(s) 25 of the drainer 24.

As depicted in FIGS. 3 and 4, the drainer 24 is moveable between a cleaning position in a lower region 19 of the apparatus 10 (FIG. 3) and a draining position in an upper region 18 of the apparatus 10 (FIG. 4). The perforated wall 25 of the drainer can have a portion thereof configured to engage at least a portion of the upper region 18 of the housing 12 to thereby position the drainer 24 in the draining position. In this manner, as discussed in more detail below, the drainer 24 can be positioned in the draining position following a cleaning operation to thereby allow the cleaning fluid 34, when present, to drain out of the drainer 24 and away from the objects 30 and to allow the objects 30 to dry. The draining position can also allow the cleaned objects to cool as necessary when heat is employed in the cleaning operation to thereby reduce the risk of injury to the user upon subsequent removal of the cleaned objects from the cleaning apparatus.

To engage the drainer 24 in the draining position, in certain embodiments of the invention, at least a portion of the upper region 18 of the housing 12 can define at least one recess 21. FIG. 2 illustrates an exemplary embodiment of the invention in which the upper region 18 of the housing 12 includes three recesses 21, positioned substantially equidistance from one another about the periphery of the opening 15. The present invention is not limited to the illustrated embodiment, and accordingly, the upper region 18 of the housing 12 can include one, two, three, or more, recesses, typically positioned equidistance from one another in a substantially uniform pattern about the inner periphery of the opening 15.

To further assist in engaging the drainer 24 in the draining position, in the exemplary embodiment illustrated, the perforated wall 25 of the drainer 24 can define at least one tab 26 dimensioned for insertion into the recess 21 to thereby position the drainer 24 in the draining position, as illustrated in FIGS. 3 and 4. The drainer 24 can include one, two, three, or more tabs, and generally includes at least one tab that will correspondingly mate with at least one of the recesses 21.

The tab 26 can be flexible or spring loaded so that the tab 26 can be moveable between at least two general positions. FIG. 4 illustrates a first tab position extending outwardly from the perforated wall 25 of the drainer 24 for engaging the recess 21 of the upper region 18 when the drainer 24 is in a draining position. FIG. 3 illustrates a second tab position substantially flush with the perforated wall 25 of the drainer 24 to thereby allow the drainer 24 to be inserted into the cleaning chamber 20.

As illustrated in FIGS. 1, 5, and 6, the drainer 24 can further include a peripheral lip 28 extending outwardly around the opening 27. The peripheral lip 28 can further include at least one handle 29 extending outwardly from the lip. The handle 29 can facilitate intentional movement of the drainer 24 by a user (e.g., when moving the drainer 24 from the cleaning position such as illustrated in FIG. 5 to the draining position such as illustrated in FIG. 6). The handle 29 can further facilitate positioning tab(s) 26 into corresponding recess(es) 21 to secure the drainer 24 in the draining position.

The apparatus of the invention can further include conventional electronic and other components as known in the art for operating an ultrasonic cleaner. For example, the apparatus can include a suitable ultrasonic power source as known in the art to generate ultrasonic energy from electrical energy, such as that received via a standard electrical cord 36 plugged into a wall outlet. Typically, the ultrasonic power source is a solid state device that converts electrical energy cycling at about 50 to 60 Hertz (Hz) to a frequency above about 18 kilohertz (KHz). Exemplary (but not limiting) discussions regarding solid state electronics include Dorf, *The Electrical Engineering Handbook, Second Ed.*, (1997) CRC Press LLC.

The ultrasonic power source can transmit the ultrasonic energy to the transducer 22, and the transducer 22 in turn can transmit the ultrasonic energy into the cleaning chamber 20, through the cleaning fluid 34 when present, and to the object 30 to be cleaned in a conventional manner. The ultrasonic energy can fall within a suitable frequency, for example, in the range of about 35 KHz to 45 KHz, although the apparatus can generate energy outside of this range.

The cleaning apparatus 10 can further include a timer (not shown) for controlling activation and deactivation of the ultrasonic power source and/or activation and deactivation of the heating element referenced above. The timer can be adjustable to allow the user to change predetermined settings, such as the desired cleaning temperature, length of the cleaning cycle, and the like. Adjustable timers useful in the apparatus of the invention are also well known and are commercially available.

Ultrasonic power sources, transducers, timers, and heating elements are well known to those of ordinary skill in the art and are commercially available. Thus, their detailed operation will not be discussed herein. Reference is made for example to various products commercially available from Codyson Electronics Co. Ltd., such as illustrated at codyson-.com.

The apparatus 10 of the invention can further include one or more visual indicators to permit the user to monitor the status of a cleaning cycle. FIGS. 1, 5, and 6 illustrate visual status indicator(s) 40*a-d*, located on an exterior portion of the side wall 16 of the housing 12. The visual status indicator(s) 40*a-d* may be utilized, for example, to indicate initiation and/or completion of a cleaning cycle. In this regard, the visual status indicator(s) 40*a-d* may further be utilized to indicate initiation of heating via the heating element and generation of ultrasonic energy. In the illustrated embodiment, for example, the apparatus can include an indicator 40*a* to indicate whether the apparatus is "on" or "off" (such as an "on/off" toggle switch); an indicator 40*b* to indicate initiation of a heating cycle; an indicator 40*c* to indicate initiation of an ultrasonic cleaning cycle; and an indicator 40*d* to indicate completion of the cleaning cycle. The visual status indicator(s) 40 may be a standard light bulb, a light emitting diode (LED), or other suitable indicator.

As illustrated in FIGS. 1, 3, 5, and 6, the base 14 of the housing 12 can further include a suction cup 37 to discourage unintentional movement of the apparatus 10. In this manner, the apparatus 10 may be secured to a flat surface via the vacuum provided by the suction cup 37 such that the apparatus 10 will not easily move due to vibration or overturn if nudged. The apparatus 10 may be intentionally moved by breaking the vacuum produced by the suction cup 37 with the aid of a suction cup access tab 38.

The present also provides a method for ultrasonically cleaning one or more objects. The present invention can be particularly useful for ultrasonically cleaning elongate objects, such as curling irons, firearms components, and other similarly shaped objects, which are oriented in a substantially vertical position.

In the method of the invention, the object(s) to be cleaned are placed into a drainer, and the drainer is inserted into a cleaning chamber of a cleaning apparatus, as illustrated in the Figures. Alternatively, the drainer can be first inserted into the cleaning chamber and the objects to be cleaned thereafter placed within the drainer.

Generally, the drainer is positioned within the cleaning chamber in a lower region thereof, referred to herein as the cleaning position, so that at least a portion, and typically the majority of, the area of the object to be cleaned in contained within the side wall of the cleaning chamber so as to maximize the effectiveness of the method. A cleaning fluid as known in the art can also be added to the cleaning chamber, either before or after inserting the drainer into the cleaning chamber.

After the objects to be cleaned and the drainer are positioned within the cleaning chamber in the cleaning position, and optionally the cleaning fluid is added, a heating element can be activated to heat the interior of the cleaning chamber, including the cleaning fluid when present, to a temperature selected to promote removal of debris from the object(s) upon the transmission of ultrasonic energy thereto. The temperature can be pre-selected or preset so that simply activating the heating element (for example, by activating an "on" switch) will initiate heating the interior of the cleaning apparatus to the preset temperature. An exemplary temperature that can be useful in the present invention is about 75° C., although temperatures less than and above this temperature can also be employed in the invention. A visual indicator can indicate that the heating element is heating the cleaning fluid to a first preset temperature. Alternatively, the cleaning cycle can be conducted in the absence of heat.

After the interior of the apparatus reaches the desired temperature, an ultrasonic energy source can be activated to generate, and in cooperation with the transducer, transmit ultrasonic energy into the cleaning chamber. A visual indicator can indicate that the transducer is transmitting ultrasonic energy into the cleaning chamber.

Generally, the ultrasonic cleaning method of the invention utilizes sound waves in a fluid medium to clean surface debris from an object. The sound waves create cavitation bubbles in a fluid medium (e.g., air, water, water-based solvent, or organic solvent). Sound waves create areas of compression (high pressure) and rarefaction (low pressure) as they travel through a medium. Cavitation bubbles form at the points of rarefaction due to the low pressure of the sound wave in the fluid. The cavitation bubbles thereafter grow under the influence of the higher pressure areas, eventually imploding. The implosion releases shock waves that contact the article being cleaned, breaking up dirt and other contaminants on the surface of the article. See the *Ultrasonic Cleaning Fundamental Theory and Application* from the PMR Systems web site (Tempe, Ariz., USA).

The step of transmitting ultrasonic energy to at least one or more objects present in a cleaning position as described herein, e.g., present in a drainer inserted into the cleaning chamber of a cleaning apparatus, is conducted under conditions sufficient to remove debris from the object(s). Ultrasonic wave frequency, cleaning cycle times, temperature, and the like, can vary, and can depend upon factors such the size and/or number of objects to be cleaned, the amount of debris to be removed from the object, the presence or absence of a cleaning solution, the chemical composition of a particular cleaning solution when present, and the like. Specific conditions sufficient to effectively remove debris from the objects to be cleaned can be readily determined by the skilled artisan, and the present invention is not limited to any particular operation temperature, cycle time, ultrasonic wave frequency, and the like.

As a non-limiting example, the frequency of the ultrasonic energy can vary, and generally can range from about 35 to about 45 KHz, although frequencies outside of this range can also be useful in the present invention. The length of time of the ultrasonic energy transmission can also vary, but the inventors have found that ultrasonic energy cycles ranging from about 10 to about 15 minutes can be effective in many applications, although cycles shorter or longer than this range can also be useful in the present invention. In addition, as noted above, the interior of the cleaning chamber, including the cleaning fluid when present, can be preheated to a preset temperature sufficient to assist in the removal of debris. The inventors have found that the combined use of a heated cleaning fluid and ultrasonic energy can be particularly effective in removing debris from the surface of the object(s), particularly objects having a relatively heavy buildup of debris.

Thereafter, the interior of the apparatus, including cleaning fluid when present, can be allowed to cool to a second temperature. Again, as with the heating step, the cooling step can include cooling the interior of the apparatus to a predetermined or preset temperature. The temperature can vary and typically is a temperature selected to allow a user to lift the drainer up to thereby position the drainer in the draining position described herein. An exemplary temperature for this step of the method is about 37° C., although the present invention is not limited to this specific temperature and temperatures less than or greater than 37° C. (for example, about 20-24° C., or about room temperature) can also useful. A visual indicator can indicate when the preset cooling temperature is reached to indicate to the user that the drainer can now be lifted from the cleaning chamber.

Engaging the drainer in the draining position can provide several benefits. The drainer is typically perforated, and the draining position allows fluid when present to readily drain from the drainer with minimal mess. In addition, because the cleaning fluid can drain back into the cleaning chamber of the apparatus, the fluid can be readily reused as desired. In addition, positioning the drainer in a draining position allows the drainer and the cleaned objects container therein to cool to an appropriate temperature selected to minimize the risk of injury that can result from contacting a heated object.

The method aspects may be controlled by a variable timer and monitored using the previously discussed visual indicators.

In the specification and the drawings, typical embodiments of the invention have been disclosed. Specific terms have been used only in a generic and descriptive sense, and not for purposes of limitation. The scope of the invention is set forth in the following claims.

That which is claimed is:

1. An apparatus suitable for ultrasonically cleaning objects, comprising:
    a housing comprising a base, a side wall extending upwardly from the base, and an upper region, wherein the upper region of the housing defines at least one recess;
    a cleaning chamber within the housing;
    a drainer for insertion into the cleaning chamber which is moveable between a cleaning position in a lower region of the apparatus and a draining position in an upper region of the apparatus, wherein the drainer comprises a perforated side wall defining at least one integral flexible tab dimensioned for insertion into the at least one recess of the upper region of the housing to position the drainer in the draining position, wherein the at least one tab is moveable from at least a first position extending outwardly from the side wall of the drainer for engaging the at least one recess of the upper region of the housing when the drainer is in a draining position, and at least a second position substantially flush with the side wall of the drainer to allow the drainer to be inserted into the cleaning chamber; and
    a transducer for transmitting ultrasonic energy into the cleaning chamber.

2. The apparatus of claim 1, wherein:
    the upper region of the housing defines at least two recesses; and the side wall of the drainer defines at least two tabs, wherein each of the tabs is dimensioned for insertion into a corresponding recess to position the drainer in the draining position.

3. The apparatus of claim 2, wherein:
the upper region of the housing defines three recesses; and
the side wall of the drainer defines three tabs, wherein each of the tabs is dimensioned for insertion into a corresponding recess to position the drainer in the draining position.

4. The apparatus of claim 1, wherein the drainer is dimensioned to accommodate at least one substantially elongate object in a substantially vertical orientation.

5. The apparatus of claim 4, wherein the side wall of the drainer defines a substantially cylindrical shape having an opening for receiving the object to be cleaned.

6. The apparatus of claim 5, wherein the drainer further comprises a peripheral lip extending outwardly around the opening.

7. The apparatus of claim 6, wherein the peripheral lip further comprises at least one tab extending outwardly from the lip.

8. The apparatus of claim 1, further comprising at least one opening in the side wall of the drainer to allow the passage of fluid into and out of the drainer.

9. The apparatus of claim 8, further comprising a plurality of openings in the side wall of the drainer to allow the passage of fluid into and out of the drainer.

10. The apparatus of claim 1, wherein the cleaning chamber is substantially cylindrical.

11. The apparatus of claim 10, wherein the substantially cylindrical cleaning chamber has a first diameter at an upper region thereof and a second diameter at a lower region thereof that is smaller than the first diameter to form a tapered cylindrical shape.

12. The apparatus of claim 1, farther comprising an ultrasonic power source for generating ultrasonic energy.

13. The apparatus of claim 12, farther comprising a timer for controlling activation and deactivation of the ultrasonic power source.

14. The apparatus of claim 13, farther comprising a heating element.

15. The apparatus of claim 14, wherein the heating element substantially surrounds the cleaning chamber.

16. The apparatus of claim 15, wherein the timer farther controls activation and deactivation of the heating element.

17. The apparatus of claim 16, wherein the timer is adjustable.

18. The apparatus of claim 14, farther comprising a cleaning fluid in the cleaning chamber, and wherein the heating element heats the cleaning fluid.

19. The apparatus of claim 1, wherein the upper region of the housing comprises a transparent material.

20. The apparatus of claim 1, further comprising at least one visual status indicator on an exterior portion of the side wall of the housing.

21. The apparatus of claim 20, comprising at least one visual indicator for indicating initiation of a cleaning cycle and at least one visual indicator for indicating completion of a cleaning cycle.

22. The apparatus of claim 21, wherein the at least one visual indicator for indicating initiation of a cleaning cycle comprises: at least one visual indicator for indicating initiation of a heating stage and at least one visual indicator for indicating generation of ultrasonic energy.

23. The apparatus of claim 1, wherein the base of the housing further comprises a suction cup to discourage unintentional movement.

24. The apparatus of claim 23, wherein the suction cup further comprises an access tab to facilitate breaking a vacuum produced by the suction cup.

25. The apparatus of claim 1, wherein the transducer is located on a bottom region of the cleaning chamber.

* * * * *